(12) United States Patent
Palmer

(10) Patent No.: US 10,531,976 B2
(45) Date of Patent: Jan. 14, 2020

(54) METHODS OF URINARY CATHETER COLLECTION AND DRAINING

(71) Applicant: Cure Medical LLC, Newport Beach, CA (US)

(72) Inventor: Timothy A. Palmer, Stillwater, MN (US)

(73) Assignee: Cure Medical LLC, Newport Beach, CA (US)

( * ) Notice: Subject to any disclaimer, the term of this patent is extended or adjusted under 35 U.S.C. 154(b) by 0 days.

(21) Appl. No.: 16/352,538

(22) Filed: Mar. 13, 2019

(65) Prior Publication Data

US 2019/0321212 A1 Oct. 24, 2019

Related U.S. Application Data

(63) Continuation of application No. 15/956,561, filed on Apr. 18, 2018.

(51) Int. Cl.
| | | |
|---|---|---|
| *A61M 39/08* | (2006.01) | |
| *A61M 25/00* | (2006.01) | |
| *A61F 5/44* | (2006.01) | |

(52) U.S. Cl.
CPC ....... *A61F 5/4404* (2013.01); *A61M 25/0017* (2013.01); *A61M 2025/0018* (2013.01); *A61M 2025/0062* (2013.01); *A61M 2202/0496* (2013.01); *A61M 2210/1085* (2013.01); *A61M 2210/1089* (2013.01)

(58) Field of Classification Search
CPC ............. A61F 5/4404; A61M 25/0017; A61M 2025/0018; A61M 2025/0062; A61M 2202/0496; A61M 2210/1085; A61M 2210/10; A61M 2210/1089; A61M 2025/0024; A61M 2025/0025; A61M 25/0026; A61M 2025/0059; A61M 25/0111; A61M 25/002
See application file for complete search history.

(56) References Cited

U.S. PATENT DOCUMENTS

| | | | |
|---|---|---|---|
| 3,699,964 A | * | 10/1972 | Ericson ............... A61F 5/44 604/33 |
| 4,246,909 A | | 1/1981 | Wu et al. |
| 5,087,251 A | * | 2/1992 | Heyman ............ A61F 5/4408 604/327 |
| 5,454,798 A | | 10/1995 | Kubalak et al. |
| 6,053,905 A | | 4/2000 | Daignault et al. |

(Continued)

*Primary Examiner* — Adam Marcetich
(74) *Attorney, Agent, or Firm* — SoCal IP Law Group LLP; Guy Cumberbatch; Steven C. Sereboff

(57) ABSTRACT

A sterile dual-purpose closed intermittent urinary catheter system that may be used as either a drain line or a collection bag. A catheter resides within an inner cavity of an extensible sheath and may be extracted from a forward end through a hub for insertion into the urethra. A valve at a rearward end of the sheath may be opened to permit the sheath to function as a drain line, or closed to permit the sheath to function as a collection bag. The sheath has an extended length substantially longer than the catheter length. The catheter is extracted from within the sheath and inserted into the urethra to start urine flow. The urine may be collected in the sheath with the valve closed, or drained straight into a toilet with the valve open. The hub may have a source of lubrication to wet the catheter as it passes through.

20 Claims, 3 Drawing Sheets

(56) References Cited

U.S. PATENT DOCUMENTS

| | | |
|---|---|---|
| 6,090,075 A | 7/2000 | House |
| 6,578,709 B1 | 6/2003 | Kavahagh et al. |
| 6,849,070 B1* | 2/2005 | Hansen ................. A61F 5/44 604/328 |
| 7,601,158 B2 | 10/2009 | House |
| 7,918,831 B2 | 4/2011 | House |
| 7,938,838 B2 | 5/2011 | House |
| 8,177,774 B2 | 5/2012 | House |
| 8,317,775 B2 | 11/2012 | House |
| 8,771,286 B2 | 7/2014 | House |
| 8,845,620 B2 | 9/2014 | House |
| 2002/0103467 A1 | 8/2002 | Kubalak |
| 2003/0018302 A1 | 1/2003 | Kavabagh et al. |
| 2004/0171979 A1 | 9/2004 | O'Neil |
| 2005/0011789 A1 | 1/2005 | Tsaur |
| 2006/0025753 A1 | 2/2006 | Kubalak et al. |
| 2007/0057222 A1* | 3/2007 | Iversen ................. F16K 3/262 251/324 |
| 2008/0051763 A1 | 2/2008 | Frojd |
| 2009/0062755 A1 | 3/2009 | Burgess et al. |
| 2009/0163884 A1 | 6/2009 | Kull-Osterlin et al. |
| 2009/0204106 A1 | 8/2009 | Golden |
| 2011/0030130 A1* | 2/2011 | Stein ................. A61F 5/4556 4/144.2 |
| 2012/0184944 A1 | 7/2012 | Tomes et al. |
| 2014/0180260 A1* | 6/2014 | Mueller ............ A61M 25/0017 604/544 |
| 2015/0000023 A1* | 1/2015 | Massey ................. A61F 5/453 4/301 |
| 2015/0000024 A1* | 1/2015 | Plath ................. A61F 5/453 4/301 |
| 2015/0126975 A1* | 5/2015 | Wuthier ............... A61F 5/4404 604/544 |
| 2016/0120688 A1* | 5/2016 | Lee ................. A61M 25/0043 604/328 |
| 2016/0193443 A1 | 7/2016 | Palmer |
| 2017/0042724 A1 | 2/2017 | Ugarte |
| 2019/0151610 A1* | 5/2019 | Fletter ............... A61M 25/0017 |

\* cited by examiner

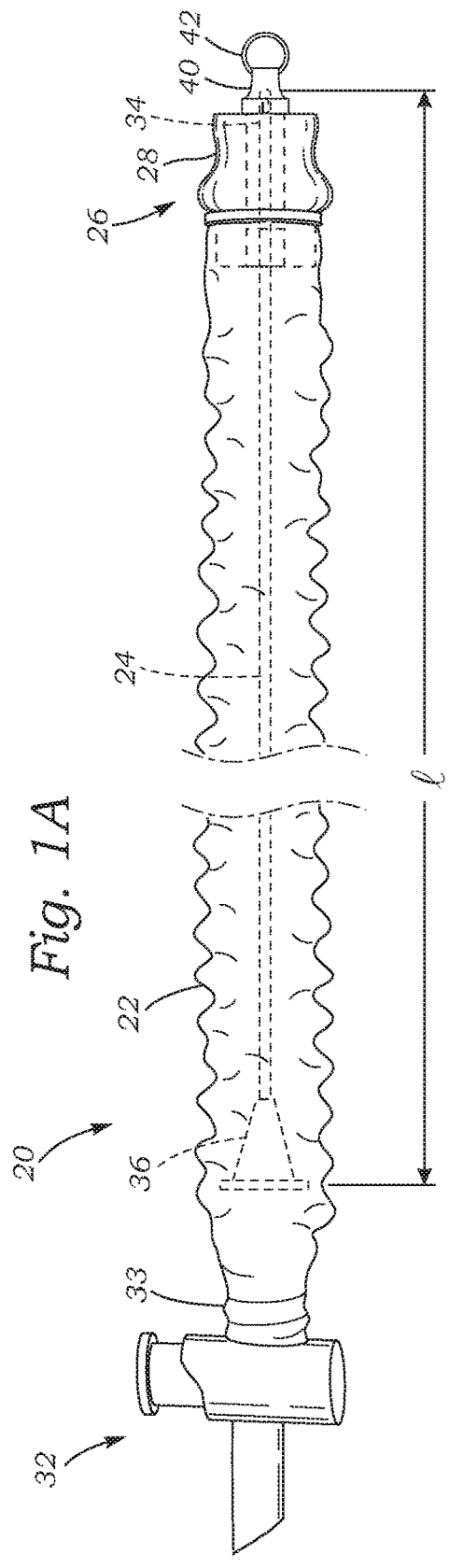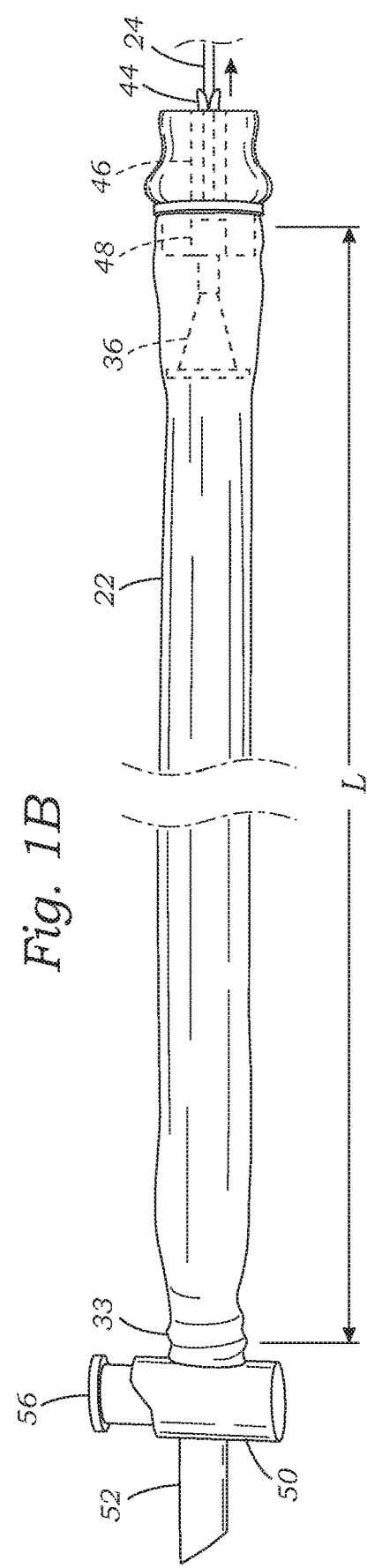

METHODS OF URINARY CATHETER COLLECTION AND DRAINING

RELATED APPLICATIONS

This patent is a continuation of application Ser. No. 15/956,561 filed Apr. 18, 2018, the disclosure of which is expressly incorporated herein by reference.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

FIELD

The present invention relates to an intermittent urinary catheter system and, more particularly, to a dual-purpose urinary catheter drain line and collection bag.

BACKGROUND

People with neurogenic bladder disorders like spinal cord injury, spina bifida or multiple sclerosis, and non-neurogenic bladder disorders like obstruction due to prostate enlargement, urethral strictures or post-operative urinary retention, need to be continuously catheterized to empty their urinary bladders. But such continuous catheterization can lead to problems like urinary tract infections (UTI), urethral strictures or male infertility. Intermittent catheterization at regular intervals avoids such negative effects of continuous long term catheterization. Research has shown that intermittent self-catheterization helps reduce urinary tract infections, control urinary leakage (incontinence) and prevent urinary tract damage.

In our highly mobile culture, the ability to have the freedom to leave home for the day or longer is an important part of life. To accommodate this need, single use intermittent urinary catheters have been developed to allow patients to perform self-catheterization. Many intermittent catheters are designed to be inserted into the bladder while the back end is suspended over a toilet or other waste receptacle. For example, the mPower Cath Hydro hydrophilic intermittent urinary catheter available from Adapta Medical of Colorado Springs, Colo. provides a sterile catheter surrounded by an elongated flexible sheath. The catheter may be extracted from one end of the sheath, which collapses in pleats, for insertion in a urethra of a user. Urine drains through the catheter and flows out an opposite end outlet to be directed into either a toilet or a collection bag. Various aspects of such catheters may be seen in U.S. Pat. Nos. 6,090,075, 8,177,774 and 8,845,620.

On the other hand, a closed system catheter is a self-contained, sterile, pre-lubricated catheter housed within a collection bag. The collection bag eliminates the need to void the urine into a receptacle or toilet, and since it is self-contained, it eliminates the need to hook up any other kind of bag or container—it is truly portable.

Despite numerous products on the market, there remains a need for a more adaptable intermittent urinary catheter system.

SUMMARY OF THE INVENTION

The present application discloses a sterile dual-purpose intermittent urinary catheter system that may be used as either a drain line or a collection bag. In one embodiment, a catheter having a length resides within an inner cavity of an extensible sheath. The sheath is sealed at both ends and the catheter may be extracted from a forward end through a hub for insertion into the urethra. A valve at a rearward end of the sheath may be opened to permit the sheath to function as a drain line, or closed to permit the sheath to function as a collection bag. The sheath has an extended length substantially longer than the catheter length.

BRIEF DESCRIPTION OF THE DRAWINGS

FIG. 1A is an elevational view of an exemplary dual-purpose intermittent urinary catheter system with an outer sheath in a collapsed configuration with a catheter housed therein;

FIG. 1B is an elevational view of the catheter system with the outer sheath in a longitudinally extended configuration and the catheter partially withdrawn therefrom;

DETAILED DESCRIPTION OF A PREFERRED EMBODIMENT

Figure 2:
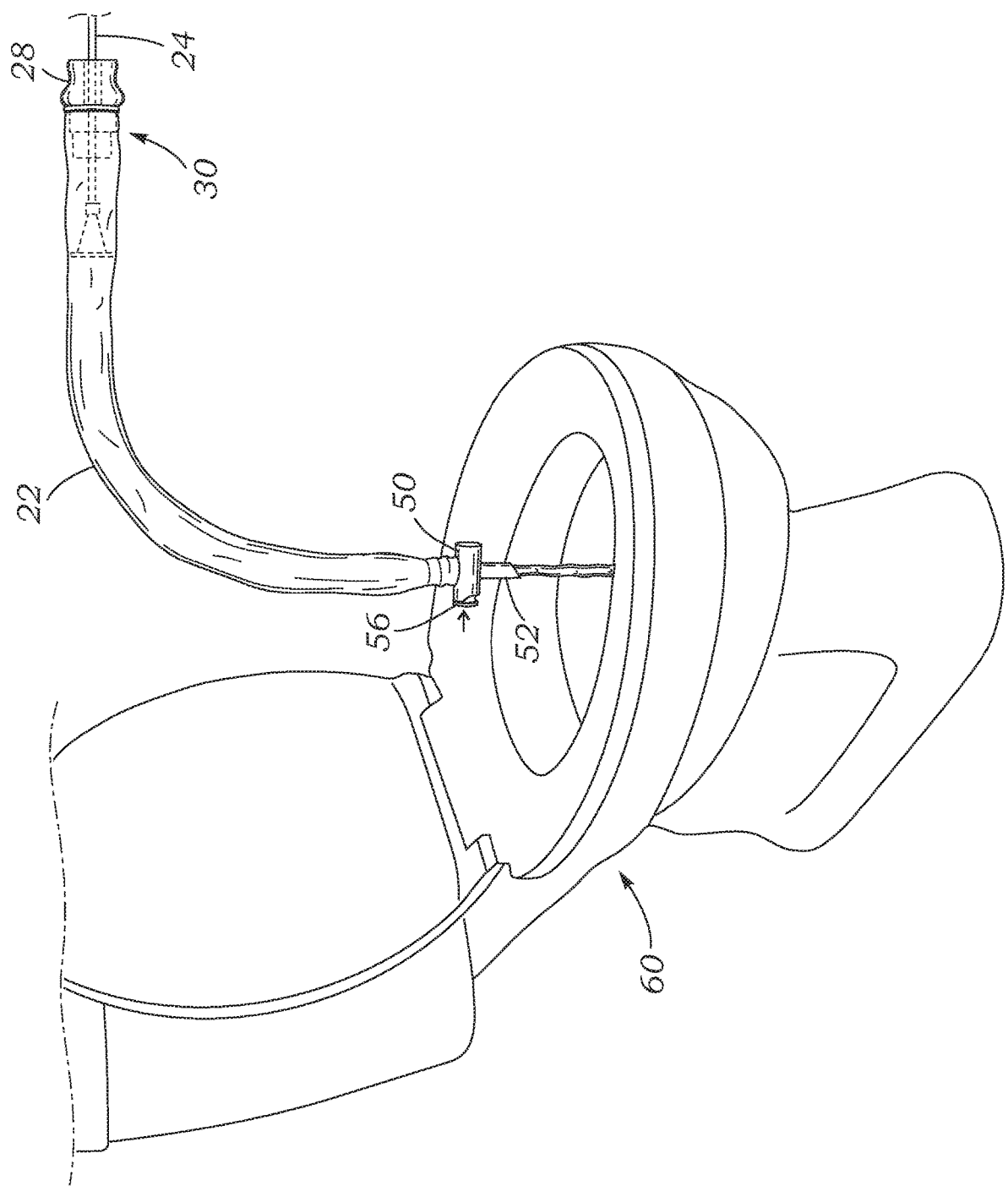
FIG. 2 is a perspective view of the system of the present application forming an open conduit and used as a drain line into a toilet.

The present application provides a closed system catheter which may be used in two ways and is thus dual-purpose. In a first mode of operation, the catheter provides a closed bag or sheath and a pre-lubricated catheter that may be extended therefrom. The user inserts the catheter into his or her urethra and thus may empty the bladder into the closed bag. In a second mode of operation, a back end of the bag may be opened so that the user can drain the flow into a convenient receptacle, such as a toilet. The bag is preferably highly extendible to provide a relatively long drain line. Conversion between the two modes is accomplished by actuating a valve incorporated into the bag.

FIG. 1A is an elevational view of an exemplary dual-purpose intermittent urinary catheter system 20 with a flexible, preferably transparent or at least translucent, outer sheath 22 and an elongated intermittent urinary catheter 24 disposed therein. The system 20 has a business or forward end 26 in the form of a rigid or semi-rigid hub 28 that as shown is closed. A rearward end 32 includes a fluid valve which is also closed as shown and will be described in greater detail below.

In the storage and shipping configuration seen in FIG. 1A, opposite ends of the substantially tubular flexible outer sheath 22 are secured to the closed ends 26, 32 such as with heat sealing, adhesive, or a stricture 33 as seen at the rear end. In its storage and shipping configuration, the flexible outer sheath 22 is collapsed or constricted longitudinally. The sheath 22 is desirably a thin polymer tube such as polyethylenes, polyamides (e.g., Nylon 11, nylon 12, nylon 6,6) polyurethanes, polyetherblockamides (e.g., PEBAX), polyesters and blends and compositions thereof which may be constricted longitudinally so as to form folds or pleats.

The intermittent urinary catheter 24 extends from a forward tip 34 to a rear funnel or enlargement 36, and has a length $\ell$ which is less than the longitudinal dimension of the sheath 22, even when constricted. The catheter 24 is typically 14 or 16 inches in length, but may be less or more as desired. As the $\ell$ of the catheter 24 is shorter than the length dimension of the sheath 22, the catheter is fully contained in a sterile manner within the sheath. Further, the assembly as shown in FIG. 1A is usually shipped in a larger outer package which displays product and instructional text, and may be easily opened and thrown away.

With reference to the forward end 26 of the system in FIGS. 1A and 1B, a sterile cap 40 with a pull ring 42 covers an opening on the front end of the hub 28. Removal of the cap 40 from the hub 28 opens the catheter system and exposes an introducer tip 44. The distal tip 34 of the catheter preferably resides just inside the introducer tip 44 when packaged. The hub 28 also may house a lubricating gel reservoir 46 and a catheter feed lock 48, both shown schematically. Prior to exiting the sheath 22, the catheter 24 passes through these components and is suitably lubricated for insertion into the urethra.

The feed lock 48 functions to permit one-way forward advancement of the catheter 24, but inhibits rearward movement thereof. Exemplary feed locks are disclosed in co-pending U.S. Patent Publication No. US 2019/0046766, the contents of which are hereby expressly incorporated by reference. It should be noted that rather than providing the lubricating gel reservoir 46, the catheter 24 may be pre-lubricated along its length, or may be provided with a dry hydrophilic coating which, when wetted, becomes lubricious. In the latter case, a small sachet of water is provided within the sheath 22 which, when ruptured, wets the catheter 24.

At the rear end of the system 20, an exemplary fluid valve has a housing 50 with a drain 52 on an outlet end, a shaft stub (not shown) over which the rear end of the sheath 22 seals, such as with the stricture 33, and an actuator 56 which opens and closes the valve. The illustrated embodiment shows a simple piston/cylinder type of valve with a plunger-type of actuator 56 that moves linearly through the tubular housing to alternately occlude and open an internal throughbore between the drain 52 and shaft stub. As shown, the plunger actuator 56 is partially retracted out of the housing 50 to close the valve and maintain the inner contents of the sheath 22 sterile. Of course, other such fluid valves are contemplated, such as a stopcock, pinch valve, slider type of actuator, etc.

In use, after removal of the cap 40 and prior to longitudinal advancement of the catheter 24 from the sheath 22, the user inserts the introducer tip 44 into the urethra (men or women). The user then advances the catheter 24 forward, as indicated by the arrow in FIG. 1B, by pinching it through the relatively flexible sheath 22 and urging it forward while holding the outlet hub 28 steady. The introducer tip 44 is sized to fit within the outer end of the urethra and made of a flexible elastomer which has petals that the catheter tip 34 spreads apart upon passage therethrough. The introducer tip 44 helps prevent any bacteria that may be around the urethra opening from contacting the catheter tip 34, which in turn helps reduce instances of infection.

Eased by the lubricated nature of the catheter 24, the user continues to slowly push the catheter 24 through the introducer tip 44 and into the urethra until the catheter reaches the bladder and urine begins to flow. The catheter 24 has one or more small eyelets (not shown) at its distal tip 34 into which the urine flows. The enlarged funnel 36 prevents complete extraction of the catheter 24 from within the sheath 22 as it abuts the internal components of the forward hub 28. Urine flows through the funnel 36 into the inner cavity of the sheath 22.

Figure 3:
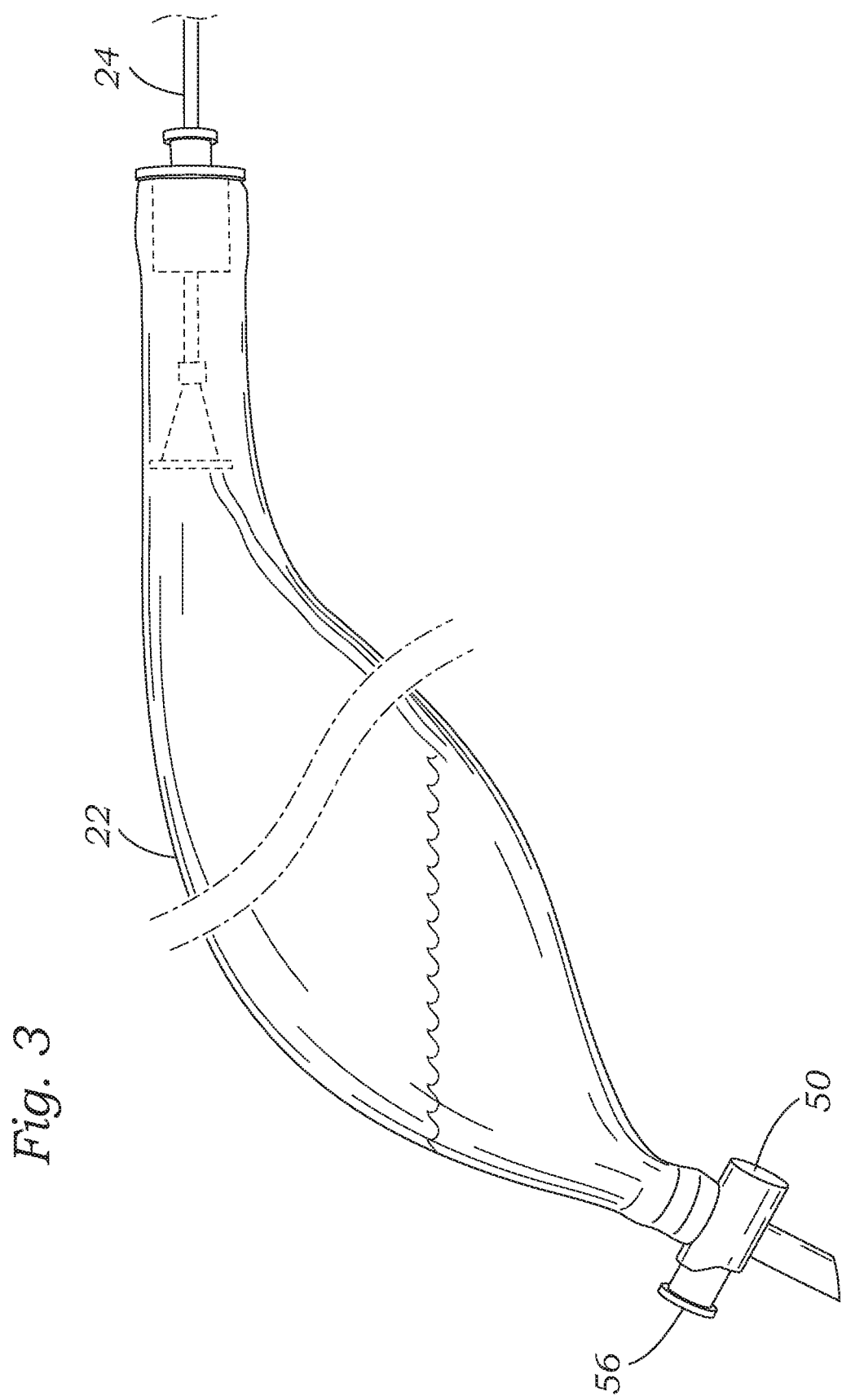
FIG. 3 is an isolated view of the system of the present application being used as a closed system with a collection bag.

FIGS. 2 and 3 are views of the catheter system 20 illustrating two options for use thereof—FIG. 2 as a drain line into a toilet, and FIG. 3 as a collection bag. In both uses, the sheath 22 is extended so that it is relatively smooth and forms either an uninterrupted flow channel or a pouch-like bag or receptacle. FIGS. 1B and 2 show the catheter 24 nearly fully withdrawn out of the sheath 22 while the sheath is extended to a full longitudinal dimension L of anywhere from 24-45 inches. In a preferred embodiment, the dimension L of the extended sheath 22 is between about 1.5-2.0 times longer than the $\ell$ of the catheter 24, or alternatively, the $\ell$ of the catheter 24 is between about ½ to ⅔ the dimension L of the extended sheath 22. For example, the $\ell$ of the catheter 24 is between about 12-16 inches if the sheath 22 has an extended dimension L of 24 inches, and between about 22-30 inches if the sheath 22 has an extended dimension L of 45 inches, with all the various combinations in between. The catheter $\ell$ is thus between about 12-30 inches.

In FIG. 2, the valve actuator 56 has been depressed as indicated to open the fluid valve. Although not shown, the user holds the hub 28 against the external opening of the urethra with the catheter 24 inserted, such as while seated on the toilet or in an adjacent seat or wheelchair. (It should be understood that the proportional size of the system 20 is somewhat enlarged for clarity.) The weight of the valve also assists to keep the drain line inserted into a toilet bowl or other receptacle. The user continues to drain urine until the flow stops, and then closes the valve. Retraction of the catheter 24 from the urethra and then into the sheath 22 provides a neat and convenient disposable product.

FIG. 3 shows the valve closed with the plunger-actuator 56 once again retracted. In this configuration, the user may initiate urine flow into the inner cavity of the sheath 22, which forms a pouch-like receptacle or collection bag. When done, the user may simply retract the catheter back into the sheath 22 and store the clean assembly until an appropriate moment to drain the urine by opening the valve. In a preferred embodiment, the length L and diameter of the sheath 22 are such that the inner volume is between about 600-2000 ml, sufficient to hold most urinary discharges.

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. Acts, elements and features discussed only in connection with one embodiment are not intended to be excluded from a similar role in other embodiments.

It is claimed:

1. A method of urinary catheter collection and draining, comprising:
    extracting a dual-purpose urinary catheter system from an outer package, the system having:
        an extensible flexible outer sheath having an extended length L, an inner cavity, a forward end and a rearward end, wherein the outer sheath is formed of a thin flexible polymer tube constricted longitudinally with folds or pleats to a partially compressed length within the outer package and configured to extend longitudinally to the extended length L by straightening out the folds or pleats;

a urinary catheter disposed within the inner cavity of the outer sheath, the catheter having a front end and $\ell$ that is less than the partially compressed length of the outer sheath;

a hub at the forward end of the outer sheath defining a throughbore sized to permit extraction of the catheter front end; and a valve at the rearward end of the outer sheath, the valve enabling conversion from a closed position to seal the inner cavity of the outer sheath at its rearward end and an open position to permit fluid flow from the inner cavity of the outer sheath at its rearward end, such that the catheter system may function as a collection bag when the valve is closed and a drain line when the valve is open;

extending the outer sheath longitudinally to the extended length L;

extracting the catheter front end from within the outer sheath through the hub;

inserting the catheter front end into a patient's urethra;

advancing the catheter until urine flows therethrough into the inner cavity of the outer sheath;

withdrawing the catheter front end from within the patient;

positioning the rearward end of the outer sheath over a toilet, the extended length L being sufficiently long so as to extend from the front end held by a user while seated adjacent and not on the toilet to the rearward end suspended over the toilet, the weight of the valve helping to keep the rearward end over the toilet; and opening the valve to the open position to permit fluid to drain from the inner cavity into the toilet.

2. The method of claim 1, wherein the steps of positioning and opening are done after the step of advancing such that urine collects in the inner cavity prior to draining.

3. The method of claim 1, wherein the steps of positioning and opening are done prior to the step of advancing such that urine drains straight through the inner cavity into the toilet.

4. The method of claim 1, wherein the inner cavity has a volume of between about 600-2000 ml.

5. The method of claim 1, wherein the hub further houses a feed lock through which the catheter passes and permits forward advancement of the catheter but inhibits rearward movement of the catheter.

6. The method of claim 1, wherein the hub further has a lubricant chamber disposed therein to lubricate the catheter as it passes through the lubricant chamber.

7. The method of claim 1, wherein the hub further includes an introducer tip on a forward end that is sized to fit within the outer end of a user's urethra and made of a flexible elastomer which has petals that the catheter front end spreads apart upon passage therethrough, and a cap with a pull ring that covers the introducer tip.

8. The method of claim 1, wherein the valve has a plunger actuator that moves linearly through a tubular housing to alternately occlude and open an internal throughbore in the valve.

9. The method of claim 1, wherein the extended length L is between about 24-45 inches and between about 1.5-2.0 times longer than the $\ell$ of the catheter.

10. The method of claim 9, wherein the $\ell$ of the catheter is between about 22-30 inches.

11. The method of claim 9, wherein the catheter $\ell$ is between about 12-30 inches.

12. A method of urinary catheter collection and draining, comprising:

providing a dual-purpose urinary catheter system within an outer package, the system having:

an extensible flexible outer sheath having an extended length L, an inner cavity, a forward end and a rearward end, wherein the outer sheath is a thin polymer tube that may be longitudinally compressed in pleats to have a partially compressed length and is configured to extend longitudinally to the extended length L by straightening out the pleats;

a urinary catheter disposed within the inner cavity of the outer sheath, the catheter having a front end and a $\ell$ between about ½ to ⅔ the extended length L of the outer sheath, wherein the $\ell$ of the catheter is shorter than the partially compressed length of the outer sheath;

a hub at the forward end of the outer sheath defining a throughbore sized to permit extraction of the catheter front end; and a valve at the rearward end of the outer sheath that may be either closed or opened to permit fluid flow therethrough, such that the catheter system may function as a collection bag when the valve is closed and a drain line when the valve is open, extracting the dual-purpose urinary catheter system from the outer package with the outer sheath in the partially compressed length;

extending the outer sheath longitudinally to the extended length L;

extracting the catheter front end from within the outer sheath through the hub;

inserting the catheter front end into a patient's urethra;

positioning the rearward end of the outer sheath over a toilet, the extended length L being sufficiently long so as to extend from the front end held by a user while seated adjacent and not on the toilet to the rearward end suspended over the toilet, the weight of the valve helping to keep the rearward end over the toilet;

opening the valve to the open position;

advancing the catheter until urine flows therethrough and straight through the inner cavity into the toilet; and withdrawing the catheter front end from within the patient.

13. The method of claim 12, wherein the extended length L is between about 24-45 inches.

14. The method of claim 12, wherein the $\ell$ of the catheter is between about 22-30 inches.

15. The method of claim 12, wherein the catheter $\ell$ is between about 12-30 inches.

16. The method of claim 12, wherein the inner cavity has a volume of between about 600-2000 ml.

17. The method of claim 12, wherein the valve has a plunger actuator that moves linearly through a tubular housing to alternately occlude and open an internal throughbore in the valve.

18. The method of claim 12, wherein the hub further houses a feed lock through which the catheter passes and permits forward advancement of the catheter but inhibits rearward movement of the catheter.

19. The method of claim 18, wherein the hub further has a lubricant chamber disposed therein to lubricate the catheter as it passes through the lubricant chamber.

20. The method of claim 18, wherein the hub further includes an introducer tip on a forward end that is sized to fit within the outer end of a user's urethra and made of a flexible elastomer which has petals that the catheter front end spreads apart upon passage therethrough, and a cap with a pull ring that covers the introducer tip.

* * * * *